US005690966A

United States Patent [19]
Bhadra et al.

[11] Patent Number: 5,690,966
[45] Date of Patent: Nov. 25, 1997

[54] PROCESS FOR THE PREPARATION OF AN EXTRACT FROM HUMAN PLACENTA CONTAINING GLYCOSPHINGOLIPIDS AND ENDOTHELIN-LIKE CONSTITUENT PEPTIDES USEFUL FOR THE TREATMENT OF VITILIGO

[75] Inventors: Ranjan Bhadra; Prajnamoy Pal, both of Calcutta, India; Rabindra Roy, Dickinson, Tex.; Ajit Kumar Dutta, Calcutta, India

[73] Assignee: Council of Scientific & Industrial Research, India

[21] Appl. No.: 734,462

[22] Filed: Oct. 17, 1996

[51] Int. Cl.$^6$ .......................... A61K 35/50; A61K 35/12; A61K 7/42
[52] U.S. Cl. .......................... 424/583; 424/520; 424/59; 514/21; 530/359; 530/851
[58] Field of Search ...................................... 424/520, 583, 424/59; 514/21; 530/359, 851

[56] References Cited

U.S. PATENT DOCUMENTS 4,507,277  3/1985  Cao et al. ................................. 424/59

OTHER PUBLICATIONS

Mal'tsev et al. Likars'ka Sparva. vol. 0, No. 7–8, pp. 123–125, Abstract enclosed 1995.
Roy et al. Intl. J. Dermatol. vol. 34, No. 1, pp. 61–66 1995.
Patel et al. Indian J. Dermatol. vol. 59, No. 5, pp. 247–250, Abstract enclosed 1993.

*Primary Examiner*—Leon B. Lankford, Jr.
*Assistant Examiner*—Christopher R. Tate
*Attorney, Agent, or Firm*—Schweitzer Cornman Gross & Bondell LLP

[57] ABSTRACT

A process for the preparation of an extract from human placenta containing glycosphingolipids and endothelin-like peptides useful for the treatment of vitiligo is disclosed.

9 Claims, No Drawings

PROCESS FOR THE PREPARATION OF AN EXTRACT FROM HUMAN PLACENTA CONTAINING GLYCOSPHINGOLIPIDS AND ENDOTHELIN-LIKE CONSTITUENT PEPTIDES USEFUL FOR THE TREATMENT OF VITILIGO

Vitiligo or 'Swetakustha', as described in ancient medical text, is a skin disfiguring phenomenon affecting about 1% of the world population compared to 3% Indians. Though not painful or lethal in nature but patients burdened with mental agony and depression due to social stigma, are extremely eager to have a wholly satisfactory-therapy for this disease. Unfortunately, vitiligo failed to respond in many oases with the therapies currently in use. So to develop a therapy satisfying the desired parameters has remained as a challenge to modern medical science.

Among the therapies mostly ill-defined, human placental extract has been claimed to be effective for vitiligo without proper justification by scientific investigation namely indication of the active components. Still the method of preparation of the extract is secretly guarded.

The hitherto known method of preparation of a hydroalcoholic extract of fresh human placenta meant for vitiligo treatment has been described in a U.S. Pat. No. 4,507,277. The process disclosed in the said patent in brief, consists of triturating human placenta cotyledons after few days of freezing in a refrigerator at about 2° to 8° C. and macerated with an absolute or about 60 to 100% wt., 95% wt., aqueous ethanol, maintaining the extraction of lipoproteins stated to be responsible for colour development in guinea pigs' nipples after 20 to 50 days of application. The active component was precipitated from the supernatant by addition of about 5 to about 20 volumes of a saturated ethanolic solution of benzoic acid. Then the precipitate was washed with the aqueous solution of benzoic acid followed by aqueous absolute acetone. The centrifugation, thereafter, was effected at about 1000 to 3000 rpm for about 10 to 30 minutes, The residue was then washed with acetone and dried in vacuum at ambient temperature. The dried residue was then redissolved in ethanol and filtered on a Sephadex TM column. The flux was 10 to 30 drops per minute and the fractions eluting a 5 to 10 mls. C/u were resolved into two peaks where second peak was stated to contain active ingredient(s). However, alcoholic extract was also mentioned as an useful preparation for application to treat the patients disfigured with vitiligo.

Regarding the efficacy of the available placental extract used in the treatment of vitiligo a lot of criticisms have been cropped up from different scientific quarters (Nordlund J. J., Halder R. Melagenina—An analysis of published and other available data. Dermatologica 1990; 181: 1–4; Goldstein E., Haberman H. F., Menon I. A., Pawlowski D. Non-psoralen treatment of vitiligo. Part II. Less commonly used and Experimental Therapies. Int. J. Dermatol. 1992; 31: 314–319) primarily for the lack of scientific evidences in respect of active principles present in it. But all the critics instead of discarding it as therapy, stressed the need for a thorough and intensive scientific investigation to look for the active components of the extracts. Some recent reports (Kojima N., Hakomori Sen-itiroth—Cell adhesion, spreading and motility of GM3-expressing cells based on glycolipid-glycolipid interaction. J. Biol. Chem. 1991; 266: 17552–17558; Imokawa G., Yada Y., Miyagishi M. Endothelin secreted from human kerationcytes are intrinsic mitogens for human melanocytes. J. Biol. Chem. 1992; 267: 24675–24680) in this respect described that glycosphingolipids and a 21-amino acid vasocons-trictor peptide, endothelin are the potent modulators of melanocyte migration as well as motility and growth promotion respectively. These are the key events in the recovery of skin pigmentation.

Accordingly, the present invention provides a process for the preparation of an extract from human placenta containing glycosphingolipids and endothelin-like constituent peptides useful for the treatment of vitiligo which comprises:

(a) chopping the whole placenta into small pieces;

(b) triturating the chopped material by known method using aqueous alcoholic solvent;

(c) extracting the whole triturated material by heating in a phased manner, first at about 40° to 50° C. for about 20 to 40 minutes and then at about 60° to 70° C. for about 5 to 15 minutes avoiding the application of direct heat:

(d) aging the triturated and heated material in the dark at room temperature minimizing exposure to air;

(e) filtering to remove comparatively larger residues/tissue debris;

(f) adjusting the concentration of alcohol present to a strength not less than 40% and not above 60% by weight using distilled water:

(g) aging the supernatant further by keeping the material for 3 to 4 days in the dark at room temperature, minimizing exposure to air;

(h) filtering through a finer filtering aid, such as Whatman No.1. filter paper packed with its shavings;

(i) keeping the supernatant thus obtained for aging to allow the finer particles to settle down;

(j) centrifuging the resulting material at about 10,000 to 14,000 rpm for about 20 to 40 minutes at about 4° to 10° C. to get a clear straw coloured extract.

The trituration in step (b) may be effected using absolute ethanol, rectified spirit, alkanols with not more than two carbon atoms and the like in an amount ranging from 85–100% by weight. The chopping and trituration may be effected at a temperature in the range of 20°–35° C. The aging of step (d) may be preferably performed for a period ranging from 36–60 hrs. The filtration of the aged material may be done using known coarse filtering system known in the art. These steps may be effected at a temperature in the range of 20° C. to 35° C. All the steps in the process are effected under normal atmospheric pressure.

In the process of the present invention, the whole placenta has been used because it has been reported that endothelin, a small vasoconstrictor peptide known to be powerful mitogenic factor for melanocyte growth and survival, occurs in the microvilli throughout the placental mass. Lipids are also distributed among all the tissue bodies. The process employs heat extraction so as to extract even small molecules known to be useful for growth and migration of pigment forming cell, melanocyte. The process avoids the use of extraneous substances such as benzoic acid and acetone. The process takes care at all steps to avoid use of excessive air exposure of the extract so that vulnerable lipid/conjugated lipid molecules are least affected.

Therefore, preparation of such extract from fresh human term placenta is a pre-requisite in order to search the active component(s), if any, present in it. Main object of the present invention is to provide an improved process for the preparation of human placental extract that upon chemical analysis is found to contain important constituents which are the active principles for the treatment of vitiligo. These active ingredients are presumed to be glycosphingolipids and endothelin-like vasoconstrictor peptides.

The heat extraction is carried out in a three-necked flask using a mechanical stirrer, a heat monitoring unit (like thermometer) and a water condenser. The flask used here may either be a water-jacketed one or it can be placed in a water bath with a temperature control device known in the art. By applying a cooling system like the water condenser mentioned above the solvent evaporation is prevented to maximize the extraction. The extract during aging and storage should be kept at room temperature and in dark preferably.

The invention as described in detail in the given examples which are provided to illustrate the invention and therefore should not be construed to limit the scope of the invention.

EXAMPLE 1

AIDS negative fresh human term placentae were collected from the Medical College hospital maternity ward. On an average the mass of a placenta was 300–350 gms. (after squeezing the excess blood associated). At first it was chopped into big pieces and then was subjected to draw out the blood still hold. Thereafter the material was triturated thoroughly for 15 minutes at room temperature in a Waring blender adding 90% ethanol, 1.2 liters for each placenta. Subsequently the whole material obtained from two placentae trituration in a typical set was taken in a 3L three-necked round-bottom flask fitted with a water condenser having guard tube of calcium chloride (fused) at the open end, a thermometer and a mechanical stirrer. The flask was half-merged in a water bath and heated till the temperature recorded by the thermometer inside the flask was close to 50°±1° C. This was maintained for 30 minutes followed by a brief heating for another 5 minutes at 60°–65° C. The entire content of the flask was then kept at room temperature for 48 hours in dark to give the aging effect while tightly corking the necks of the flask. It minimized the exposure of the material to air. Large tissue mass was then filtered through a coarse filtering aid (cheese cloth or the like) and the filtrate thus collected was preserved In a 4 L (conical) flask, The alcohol concentration of the extract (presumably close to 85–90% v/v) was then adjusted approximately to 60% (v/v) by the addition of water (calculated after the measurement of the extract). The volume of the extract obtained from two placentae was nearly 3.5 liters. The flask was then sealed tightly to minimize the exposure to air and kept in dark at room temperature for another 48–60 hours in order to further aging of the material. The finer particles as appeared after such aging were settled down at the bottom of the container. It was filtered out through a finer filter aid, such as Whatman No. 1 filter paper packed with its shavings on a Buchner funnel. The filtrate thus obtained was collected in another 4 L (conical) flask and aged for the third time for a period of 24 hours under the conditions as described before. Finally the material was centrifuged at 10,000 rpm for 30 minutes using a (Beckman) sorvall cengtrifuge. The clear straw coloured extract thus obtained as supernatant was separated and collected as finished product and used for bottling. The final volume of the extract was about 3.48 liters. For better storage of the product amber colour bottle was used in packing and the packed material was stored in a cool and dark place at room temperature.

| Materials and Conditions employed | |
| --- | --- |
| No. of placenta processed at a time | Two |
| Average mass of a placenta | 325 gms |
| Alcohol conc. during trituration | 90% (v/v) |
| Vol. of alcohol used per placenta | 1.2 liters |
| Extraction temperature and time | First at 50° ± 1° C. for 30 minutes and then at 60° ± 1° C. for 5 minutes |
| Duration and condition maintained during first aging | 48 hours in dark at room temperature by tight corking |
| Filtering aid to remove large tissue mass | Coarse filtering aid (cheese cloth or the like) |
| Final alcohol conc. after adjustmnt with water | approximately 60% (v/v) |
| Duration and condition maintained during second aging | 48–60 hours in dark at room temperature by tight corking |
| Filtering aid to remove finer particles | Whatman No.1 filter paper packed with its shavings |
| Duration and condition maintained during third(final) aging | 24 hours in dark at room temperature by tight corking |
| Speed, duration and temperature during centrifugation | 10,000 rpm; 30 minutes; 2–4° C. |
| Final volume of the extract obtained | 3.48 liters (approximately) |
| Storage | In amber colour bottle and in cool and dark place at room temperature |

| Gross Composition Analysis (for quality control) | |
| --- | --- |
| Components | Conc. in the alcohol extract (mg/ml) |
| Acetone soluble peptides* | 0.002 |
| Acetone precipitable peptides/ small proteins | 0.008 |
| Free sialic acid | 0.009 or (9 µg/ml) |
| Bound sialic acid | 0.008 or (0.8 µg/ml) |
| Total lipids** | 0.362 |
| Total carbohydrates | 0.141 |
| Total phosphorous | 0.016 |
| Minor Components detected | Vitamin B6 and D, Nucleotides, Traces of amino acids like Asparagine, Threonine, Valine, Tryptophan, Phenylalanine. Progesterone and Oestrogens (in ng. to pg.). Glucocorticoids (about 100 ng/ml). |

*Bio-assay of this fraction clearly indicated a vasoconstrictor property similar to that of endothelin peptide, known as an indispensible agent for melanocyte growth.
**Lipids upon further analysis showed glycosphingolipids and other polar and non-polar lipids. Sphingolipids have been reported as an agent for adhesion, spreading and motility of skin cells, melanocyte.

All the estimations and analysis were performed according to the standard published methods. For example, protein estimation by Lowry method, Carbohydrates by Orcinol-$H_2SO_4$ method, Sialic acids by TBA assay method, Phosphorous by Ames method, Lipids by Phosphovanillin-$H_2SO_4$ method etc.).

EXAMPLE 2

The details of the process are almost same as described under example 1 for the preparation of the placental extract. Varying parameters have been used only in case of material types and conditions of the process. This includes minor quantitative variations in components of the extract. The details of the parameters of the process conditions and composition of the extract are given below:

| Materials and Conditions employed: | |
| --- | --- |
| No. of placenta processed at a time | Two |
| Average mass of a placenta | 348 gms |
| Alcohol conc. during trituration | 95% (v/v) |
| Vol. of alcohol used per placenta | 1.25 liters |
| Extraction temperature and time | First at 45° ± 1° C. for 30 minutes and then at 65 ± 1° C. for 10 minutes |
| Duration and condition maintained during first aging | 52 hours in dark at room temperature (27° C.) by tight corking. |
| Filtering aid to remove large | Course filtering aid (Nylon cloth |

| | |
|---|---|
| tissue mass | or the like) |
| Final alcohol conc. after adjustment with water | Approximately 58% (v/v) |
| Duration and condition maintained during second aging | 60 hours in dark at room temperature (27° C.) by tight corking |
| Filtering aid to remove finer particles | Whatman No.1 filter paper packed with its shavings |
| Duration and condition maintained during second aging | 30 hours in dark at room temperature by tight corking |
| Speed duration and temperature during centrifugation | 10,000 rpm; 30 minutes; 2–4° C. |
| Final volume of the extract obtained | 4.1 liters (approximately) |
| Storage | In amber colour bottle and in a cool and dark place at room temperature |

| Gross Composition Analysis (for quality control) | |
|---|---|
| Components | Conc. in the alcohol extract (mg/ml) |
| Acetone soluble peptides* | 0.0018 |
| Acetone precipitable peptides/ small proteins | 0.009 |
| Free sialic acid | 0.011 or (11 µg/ml) |
| Bound sialic acid | 0.0005 or o.5 µg/ml) |
| Total lipids** | 0.355 |
| Total carbohydrates | 0.135 |
| Total phosphorous | 0.022 |
| Minor components detected | Vitamin B6 and D, Nucleosides, Traces of amino acids like Asparagine, Threonine, Valine, Tryptophan and Phenylalanine. Progesterones and Oestrogens (in ng. to pg.). Glucocorticoids (about 110 ng/ml). |

*Bio-assay of this fraction clearly indicated a vasoconstrictor property similar to that of endothelin peptide, known as indispensible agent for melanocyte growth.
**Lipids upon further analysis showed glycosphingolipids and other polar and non-polar lipids. Sphingolipids have been reported as an agent for adhesion, spreading and motility of skin cells, melanocyte.

(All the estimations and analysis were performed according to the standard published methods. For examples, Protein estimation by Lowry method, Carbohydrates by Orcinol-$H_2SO_4$ method, Sialic acids by TBA assay method, Phosphorous by Ames method, Lipids by Phosphovanillin-$H_2SO_4$ method etc.

EXAMPLE 3

The details of the process are same as described under example 1 for the preparation of the placental extract. Varying parameters have been used only in case of material types and conditions of the process. This includes minor quantitative variations in components of the extract. The details of the parameters and composition of the extract are given below:

| Materials and Conditions employed | |
|---|---|
| No. of placenta processed at a time | Two |
| Average mass of a placenta | 330 gms |
| Alcohol conc. during trituration | 92% (v/v) |
| Vol. of alcohol used per placenta | 1.22 liters |
| Extraction temperature and time | First at 50 ± 1° C. for 40 minutes and then at 60 ± 1° C. for 10 minutes |
| Duration and condition maintained during first aging | Same as in example-2 |
| Filtering aid to remove large tissue mass | Fine absorbent cotton pad |
| Final alcohol conc. after adjustment with water | approximately 60% (v/v) |
| Duration and condition maintained during second aging | Same as in example-2 |
| Filtering aid to remove finer particles | Same as in example-2 |
| Duration and condition maintained during third(final) aging | Same as in example-2 |
| Speed, duration and temperature during centrifugation | Same as in example-2 |
| Final volume of the extract obtained | 3.48 liters (approximately) |
| Storage | Same as in examaple-2 |

| Gross Composition Analysis (for quality control) | |
|---|---|
| Components | Conc. in the alcohol extract (mg/ml) |
| Acetone soluble peptides* | 0.0015 |
| Acetone precipitable peptides/ small proteins | 0.0025 |
| Free sialic acid | 0.004 or (4 µg/ml) |
| Bound sialic acid | 0.004 or (4 µg//ml) |
| Total lipids** | 0.350 |
| Total carbohydrates | 0.138 |
| Total phosphorous | 0.014 |
| Minor Components detected | Vitamin B6 and D, Nucleosides, Traces of amino acids like Asparagine, Threonine, Valine, Tryptophan, Phenylalanine. Progesterones and Oestrogens (in ng. to pg.). Glucocorticoids (about 100 ng/ml). |

*Bio-assay of this fraction clearly indicated a vasoconstrictor property similar to that of endothelin peptide, known as an indispensible agent for melanocyte growth.
**Lipids upon further analysis showed glycosphingolipids and other polar and non-polar lipids. Sphingolipids have been reported as an agent for adhesion, spreading and motility of skin cells, melanocyte.

(All the estimations and analysis were performed according to the standard published methods. For examples, Protein estimation by Lowry method, Carbohydrates by Orcinol-$H_2SO_4$ method, Sialic acids by TBA assay method, Phosphorous by Ames method, Lipids by Phosphovanillin-$H_2SO_4$ method etc.)

EXAMPLE 4

The details of the process are same as described under example 1 for the preparation of the placental extract. Varying parameters have been used only in case of material types and conditions of the process. This includes minor quantitative variations in components of the extract. The details of the parameters and composition of the extract are given below:

| Materials and Conditions employed | |
|---|---|
| No. of placenta processed at a time | Two |
| Average mass of a placenta | 340 gms |
| Alcohol conc. during trituration | 87% (v/v) |
| Vol. of alcohol used per placenta | 1.24 liters |
| Extraction temperature and time | First at 45° ± 1° C. for 40 minutes and then at 63 ± 1° C. for 5 minutes |
| Duration and condition maintained during first aging | Same as in example-2 |
| Filtering aid to remove large tissue mass | Same as in example-2 |
| Final alcohol conc. after adjustment with water | Approximately 56% (v/v) |
| Duration and condition maintained during second aging | Same as in example-2 |
| Filtering aid to remove finer particles | Same as in example-2 |
| Duration and condition maintained during third(final) aging | Same as in example-2 |

-continued

| Speed, duration and temperature during centrifugation | Same as in example-2 |
|---|---|
| Final volume of the extract obtained | 4.1 liters (approximately) |
| Storage | Same as in example-2 |

Gross Composition Analysis (for quality control)

| Components | Conc. in the alcohol extract (mg/ml) |
|---|---|
| Acetone soluble peptides* | 0.0017 |
| Acetone precipitable peptides/ small proteins | 0.002 |
| Free sialic acid | 0.008 or (8 μg/ml) |
| Bound sialic acid | 0.001 or (1 μg/ml) |
| Total lipids** | 0.352 |
| Total carbohydrates | 0.132 |
| Total phosphorous | 0.020 |
| Minor Components detected | Vitamin B6 and D, Nucleosides, Traces of amino acids like Asparagine, Threonine, Valine, Tryptophan, Phenylalanine. Progesterones and Oestrogens (in ng. to pg.). Glucocorticoids (about 120 ng/ml). |

*Bio-assay of this fraction clearly, indicated a vasoconstrictor property similar to that of endothelin peptide, known as an indispensible agent for melanocyte growth.
**Lipids upon further analysis showed glycosphingolipids and other polar and non-polar lipids. Sphingolipids have been reported as an agent for adhesion, spreading and motility of skin cells, melanocyte.

(All the estimations and analysis were performed according to the standard published methods. For examples, Protein estimation by Lowry method, Carbohydrates by Orgcinol-$H_2SO_4$ method, Sialic acid by TBA assay method, Phosphorous by Ames method, Lipids by Phosphovanillin-$H_2SO_4$ method etc.)..

Studies on pigmenting activity of the extract in animal model (a) Guinea pig model:

20 drops of the extract was applied at the areola regions of male immature white guinea pigs (weight 205–250 gms) twice daily with 15 minutes duration in each application for at least 2 months without any intermission. The region of application was exposed to IR (230 V/150 W) for 15 minutes after each application from a distance of 45 cms. The result was quite promising with darkening of the area and hypertropy of the nipples as reported in the model experiment (J. Invest. Dermatol. 1953, 20: 385–399).

The weight of the guinea pig used is very critical and much below 200 gms younger guinea pig experiences tremendous alcoholic shock risking their survival even when 50–60% alcohol alone is applied topically on them.

| Approximate weight of guinea pig (in gms) | Recording of darkening effect (in months) Extract from | | | |
|---|---|---|---|---|
| | Example 1 | Example 2 | Example 3 | Example 4 |
| 205 | 2.0 | 2.0 | 2.5 | 2.0 |
| 220 | 2.0 | 2.5 | 2.5 | 2.5 |
| 225 | 2.5 | 2.0 | 2.0 | 2.5 |
| 240 | 2.5 | 2.5 | 3.0 | 2.0 |
| 250 | 2.8 | 3.0 | 3.0 | 2.5 |

(b) Mouse model (C57/BL6):

A portion of the mouse body coat with brownish hair (this strain of mouse shows their coat colour fading from deep black to brownish grey on aging and considerably adult mice with brown coat colour is used as animal model for vitiligo) was removed by shavings end the clean shaved area was chosen for application of the extract. Total 15 drops of the extract was applied on this cleanly shaved areas with gentle rubbing. After the application, the mice were subjected to IR exposure as in the case of guinea pig end the application was performed twice daily. Between 5 and 6 weeks clear dark black hairs/skin—spots started to reappear while the peripheral hairs continued to show further fading of colour to lighter brown.

| No. of mouse | Region of application | Recording of reappearance of black hair in the shaved region (in weeks) extract from | | | |
|---|---|---|---|---|---|
| | | Example 1 | Example 2 | Example 3 | Example 4 |
| 4 | Dorsal side | 5 | 5 | 6 | 5 |
| 3 | Lateral side | 5 | 5 | 5 | 6 |

Advantages of the invention:

The preparation of the hydroalcoholic extract according to the process of the present invention is very simple, The extract obtained is quite easy to apply on patients' skin topically, if desired, Both alcohol and placenta (a hospital waste) are adequately available raw materials in the country. No special chemicals or apparatus is required to carry out the process. Since process is very economical it is highly encouraging for taking up as commercial venture. No special storage facility or transportation of the material is necessary. It is easy to develop quality control parameters after identification of the active constituents by standard procedures. As it is a topical preparation, so it will not .have to go through crucial clinical trial procedures which are necessary for an oral or parental therapy.

We claim:

1. A process for the preparation of an extract from human placenta containing glycosphingolipids and endothelin-like peptides useful for the treatment of vitiligo which comprises:

(a) chopping the whole placenta into small pieces;

(b) triturating the chopped material by a known method using an aqueous solvent;

(c) extracting the whole triturated material by heating in a phased manner, first at about 40°–50° C. for about 20–40 minutes and then at about 60°–70° C. for about 5–15 minutes, avoiding the application of direct heat;

(d) aging the triturated and heated material in the dark for a suitable period of time at room temperature while minimizing exposure to air;

(e) filtering through a coarse filtering aid to remove larger residues/tissue debris;

(f) depending on the solvent concentration, adjusting said concentration to a strength of not less than 40% and not more than 60% by weight using distilled water;

(g) aging the supernatant further by keeping the material for a suitable period of time in the dark at room temperature while minimizing exposure to air;

(h) filtering through a finer filtering aid;

(i) aging the supernatant thus obtained to allow finer particles to settle down and (j) centrifuging the resultant material to get the clear straw colored extract.

2. A process as claimed in claim 1 wherein the trituration in step (b) is effected using dehydrated alcohol, rectified spirit, aqueous alkanol with two carbon atoms and the like.

3. A process as claimed in claim 1 wherein the chopping and trituration is effected at a temperature in the range of 20°–35° C.

4. A process as claimed in claim 1 wherein the concentration of the alcoholic solvent used for the trituration in step (b) ranges from 85–100% by weight.

5. A process as claimed in claim 1 wherein the aging in step (b) is effected for a period of about 36–60 hours, and the aging in step (g) is effected for a period of about 2–4 days.

6. A process as claimed in claim 1, wherein the filtration steps are effected at a temperature in the range of 20°–35° C.

7. A process as claimed in claim 1 wherein the process is effected at normal atmospheric pressure.

8. A process as claimed in claim 1 wherein the finer filtering aid in step (h) is Waltman No. 1 filter paper packed with its shavings.

9. A process as claimed in claim 1 wherein the centrifuging in step (j) is effected at about 10,000–14,000 rpm for about 20–40 minutes at a temperature of about 2°–10° C.

* * * * *